United States Patent [19]
Douk et al.

[11] Patent Number: 6,027,474
[45] Date of Patent: Feb. 22, 2000

[54] HYDRAULIC EXCHANGE CATHETER

[75] Inventors: Nareak Douk, Lowell; William A. Berthiaume, Hudson, both of Mass.

[73] Assignee: Medtronic AVE, Inc., Santa Rosa, Calif.

[21] Appl. No.: 09/164,006

[22] Filed: Sep. 30, 1998

[51] Int. Cl.$^7$ .................................................. A61M 37/00
[52] U.S. Cl. ............................ 604/95; 604/528; 604/534; 606/191
[58] Field of Search ...................... 604/95, 96, 158, 604/159, 161, 528, 533, 534, 535, 102, 164, 264, 523, 905; 606/191, 192, 194, 193; 600/433–435

[56] References Cited

U.S. PATENT DOCUMENTS

| | | |
|---|---|---|
| 3,583,404 | 6/1971 | McWhorter ............................. 128/349 |
| 3,592,192 | 7/1971 | Harautuneian . |
| 3,610,240 | 10/1971 | Harautuneian . |
| 3,896,815 | 7/1975 | Fettel et al. . |
| 4,564,014 | 1/1986 | Fogarty et al. . |
| 4,715,378 | 12/1987 | Pope, Jr. et al. . |
| 4,732,152 | 3/1988 | Wallstéin et al. . |
| 4,848,343 | 7/1989 | Wallstéin et al. . |
| 4,875,480 | 10/1989 | Imbert . |
| 5,002,559 | 3/1991 | Tower . |
| 5,112,304 | 5/1992 | Barlow et al. . |
| 5,152,277 | 10/1992 | Honda et al. . |
| 5,171,297 | 12/1992 | Barlow et al. . |
| 5,334,153 | 8/1994 | McIntyre et al. . |
| 5,370,617 | 12/1994 | Sahota ..................................... 604/102 |
| 5,372,592 | 12/1994 | Gambale . |
| 5,387,226 | 2/1995 | Miraki . |
| 5,389,087 | 2/1995 | Miraki . |
| 5,395,332 | 3/1995 | Ressemann et al. . |
| 5,407,432 | 4/1995 | Solar . |
| 5,409,459 | 4/1995 | Gambale . |
| 5,413,560 | 5/1995 | Solar . |
| 5,425,711 | 6/1995 | Ressemann et al. . |
| 5,443,456 | 8/1995 | Alliger et al. . |
| 5,447,503 | 9/1995 | Miller . |
| 5,451,233 | 9/1995 | Yock . |
| 5,462,530 | 10/1995 | Jang . |
| 5,466,222 | 11/1995 | Ressemann et al. . |
| 5,484,409 | 1/1996 | Atkinson et al. . |
| 5,489,271 | 2/1996 | Anderson . |
| 5,492,532 | 2/1996 | Ryan et al. . |
| 5,501,227 | 3/1996 | Yock . |
| 5,507,731 | 4/1996 | Hernandez et al. . |
| 5,514,093 | 5/1996 | Ellis et al. . |
| 5,549,551 | 8/1996 | Peacock, III et al. . |
| 5,558,635 | 9/1996 | Cannon . |
| 5,569,184 | 10/1996 | Crocker et al. ............................ 604/53 |
| 5,571,087 | 11/1996 | Ressemann et al. . |
| 5,579,779 | 12/1996 | Humphrey . |
| 5,591,194 | 1/1997 | Berthiaume . |
| 5,598,844 | 2/1997 | Diaz et al. . |
| 5,607,406 | 3/1997 | Hernandez et al. . |
| 5,609,583 | 3/1997 | Hakki et al. .............................. 604/53 |
| 5,645,533 | 7/1997 | Blaeser et al. . |
| 5,658,251 | 8/1997 | Ressemann et al. . |
| 5,658,309 | 8/1997 | Berthiaume et al. . |
| 5,674,287 | 10/1997 | Slepian et al. ............................ 623/11 |
| 5,676,654 | 10/1997 | Ellis et al. . |
| 5,693,021 | 12/1997 | Diaz et al. . |
| 5,779,671 | 7/1998 | Ressemann et al. . |
| 5,840,066 | 11/1998 | Matsuda et al. .......................... 604/96 |

Primary Examiner—Wynn Wood Coggins
Assistant Examiner—Eric Kline
Attorney, Agent, or Firm—Sterne, Kessler, Goldstein & Fox P.L.L.C.

[57] ABSTRACT

The invention relates to a catheter device and method of use for exchanging a catheter having a full-length guidewire lumen over a conventional-length guidewire without the use of a guidewire extension or an exchange wire. The catheter device includes an elongated shaft defining an inflation lumen and a guidewire lumen extending longitudinally throughout its length, and a hydraulic exchange lumen extending from the proximal end of the shaft and terminating proximal the distal end of the shaft, wherein the hydraulic exchange lumen is in fluid communication with the guidewire lumen. A balloon is coupled to the distal section of the shaft and is in fluid communication with the inflation lumen. A flow guiding member is disposed within the guiding catheter and functions to redirect the distal flow of pressurized fluid traveling through the hydraulic exchange lumen in a proximal direction through the guidewire lumen.

13 Claims, 3 Drawing Sheets

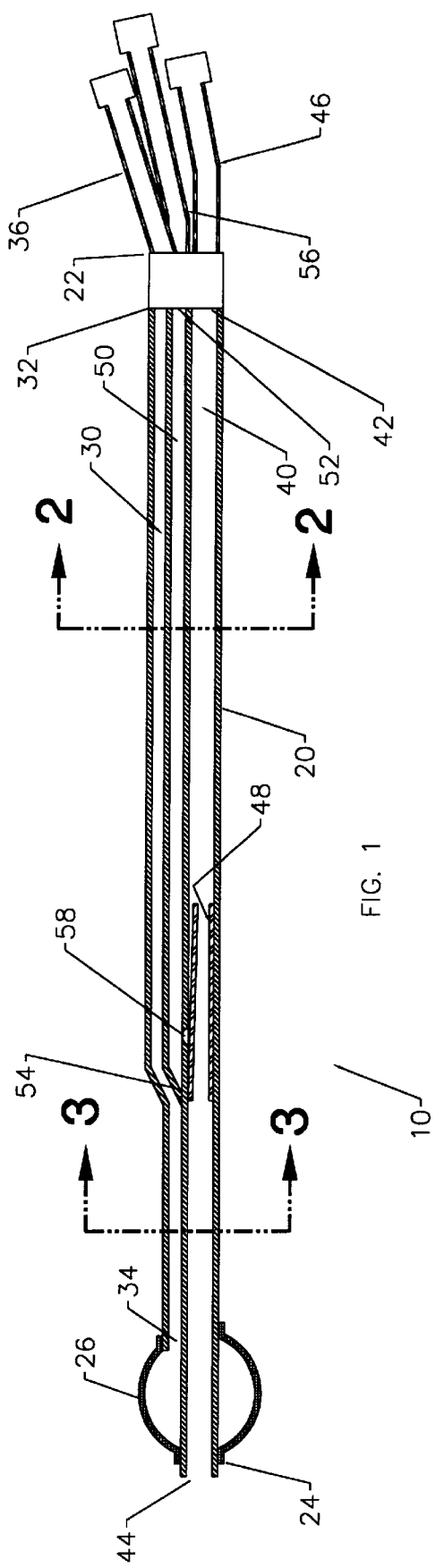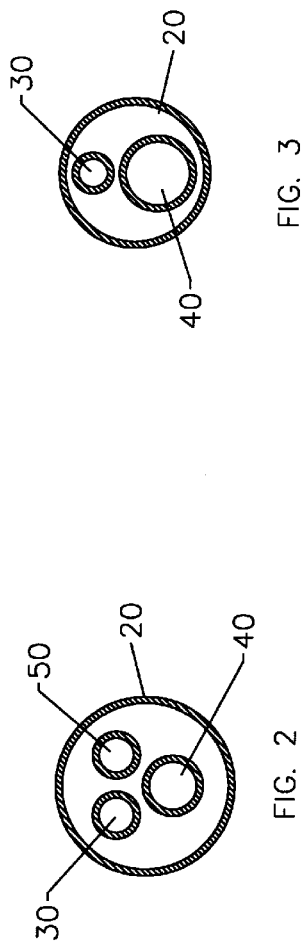
FIG. 1
FIG. 2
FIG. 3

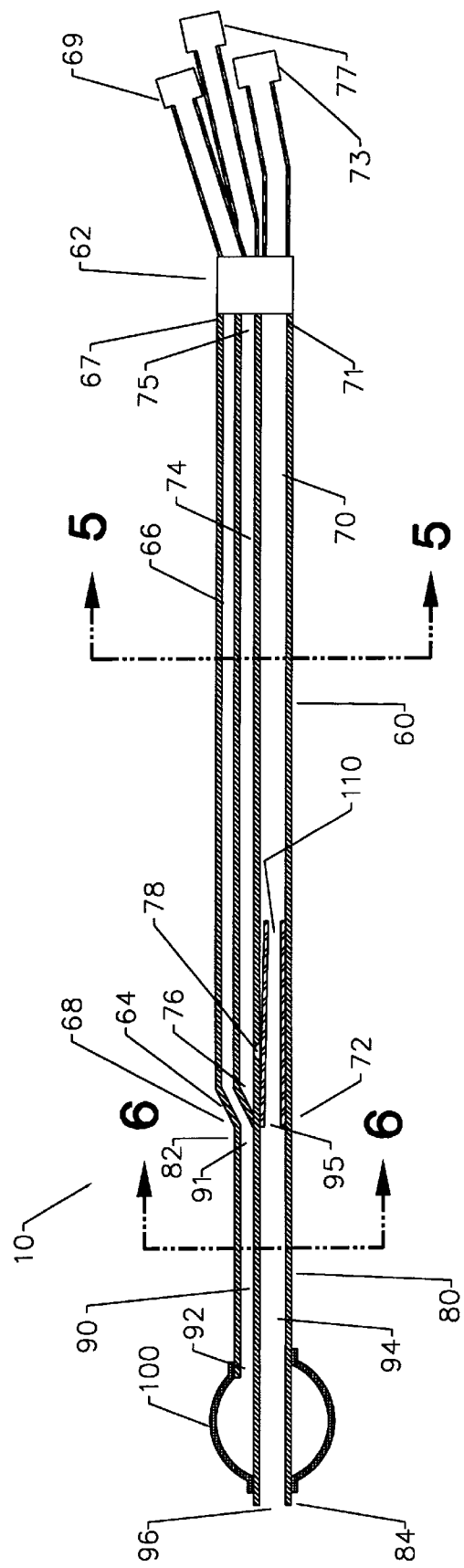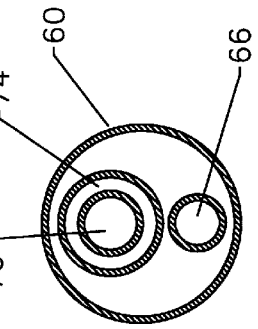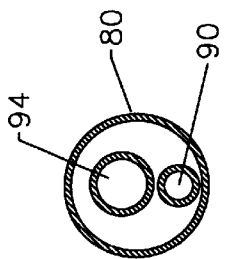

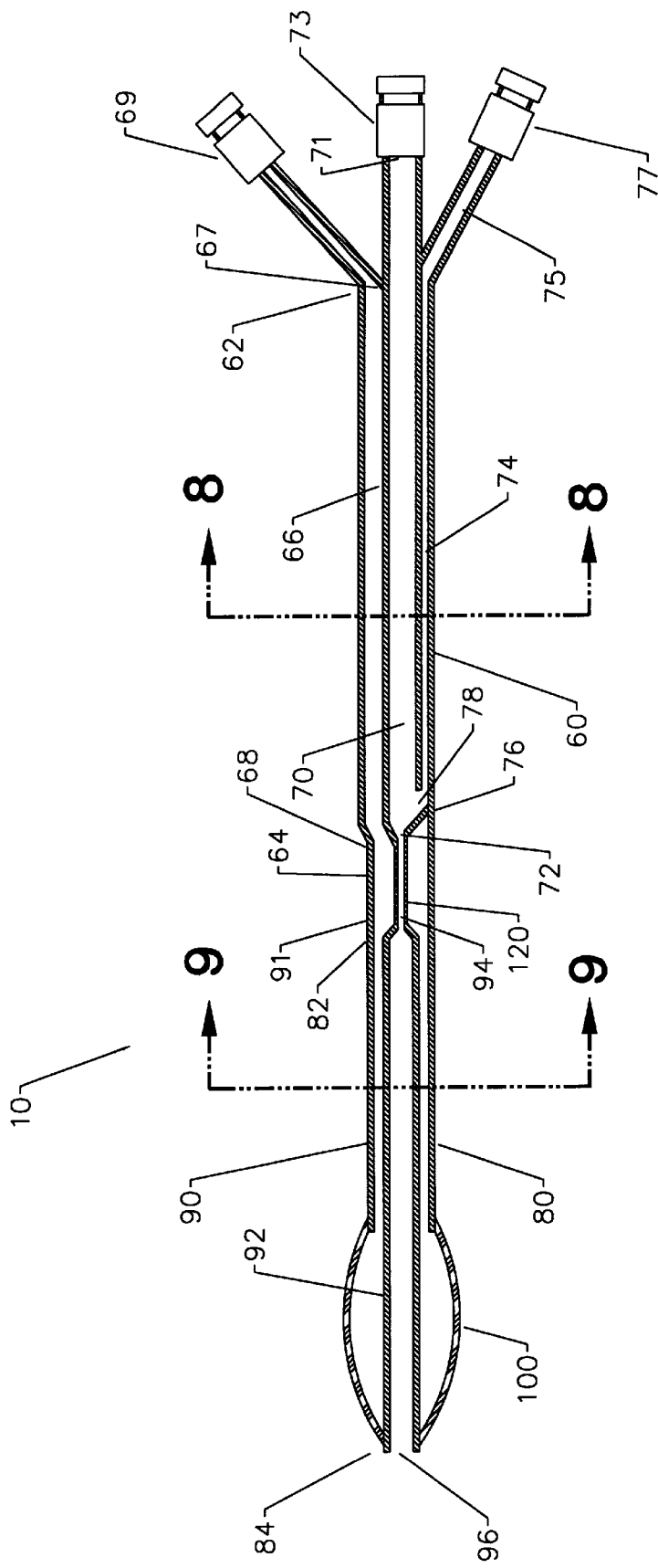
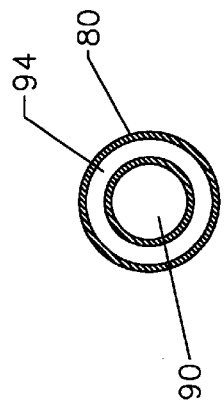
FIG. 7
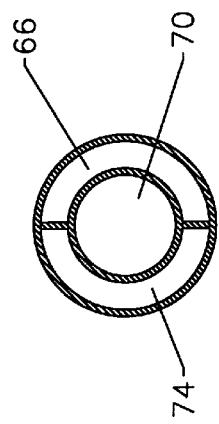
FIG. 8
FIG. 9

HYDRAULIC EXCHANGE CATHETER

FIELD OF THE INVENTION

The present invention relates to catheter systems employed in intravascular procedures. More particularly, the present invention relates to a catheter device and method of use for facilitating the exchange of a catheter having a full-length guidewire lumen over a conventional-length guidewire without the use of guidewire extensions or exchange wires.

BACKGROUND OF THE INVENTION

Various balloon catheter designs have been developed for use in a wide range of medical procedures, such as angioplasty dilatation, stent delivery and localized drug delivery. One of the basic catheter designs for use in these medical procedures is known as an "over-the-wire" balloon catheter.

Conventional "over-the-wire" angioplasty dilatation catheters generally comprise an elongated catheter shaft having a proximal end and a distal end. The catheter includes an expandable balloon located at the distal end of the catheter tube. The catheter shaft typically defines an inflation lumen in fluid communication with the interior of the balloon which extends longitudinally to the proximal end of the catheter shaft. The catheter shaft also defines a separate guidewire lumen which extends longitudinally from the catheter shaft proximal end through the catheter shaft distal end.

Conventional "over-the-wire" angioplasty dilatation catheters are typically guided into position within the patient's vasculature through the use of a flexible guidewire having a diameter of approximately 0.010 to 0.018 inches and a length of about 180 centimeters. The distal end of the guidewire is extremely flexible so that it may be routed through the convoluted arterial pathway to the site of the stenosis. Once the distal portion of the guidewire is positioned across the treatment site, a conventional "over-the-wire" catheter may be threaded onto the guidewire by inserting the guidewire proximal end through the catheter guidewire lumen. With the balloon in a deflated state, the catheter is advanced through the patient's vasculature over the guidewire until the balloon is positioned across the treatment site. When it is desired to inflate the balloon, pressurized inflation fluid is injected into the proximal end of the inflation lumen via a syringe or other suitable pressure infusion device. As the pressurized inflation fluid travels through the inflation lumen and into the balloon, the balloon radially expands such that it presses against and opens the occlusion at the treatment site.

During a catheterization procedure, it may be necessary to thread a catheter on or off an indwelling catheter, or exchange an indwelling catheter for another catheter over an indwelling guidewire. To advance or withdraw a catheter over an indwelling guidewire, the physician must be able to grip the proximal portion of the guidewire extending outside the patient's body to maintain the position of the distal portion of the guidewire across the treatment site. However, the length of a conventional over-the-wire catheter, typically on the order of 135 centimeters, is greater than the length of the proximal portion of a standard guidewire which protrudes out the patient. Accordingly, it is necessary to extend the guidewire a sufficient distance outside the patient so that the physician may maintain his or her grip on the proximal portion of the guidewire while threading an over-the-wire catheter on or off an indwelling catheter. The additional length of guidewire needed is typically provided through the use of a guidewire extension which is temporarily "linked" or attached to the proximal end of the guidewire. Once the catheter has been threaded onto the guidewire extension and advanced over the guidewire through the patient's vasculature, the guidewire extension may be detached from the guidewire.

Alternatively, a long exchange wire on the order of 300 centimeters may first be guided through the patient's vasculature such that its distal portion is positioned across the treatment site. The catheter may then be advanced over the exchange wire without disturbing the position of the distal portion of the wire. After the catheter balloon is positioned at the treatment site, the exchange wire may be removed from the guidewire lumen and replaced with a shorter, easier to handle guidewire.

Therefore, there exists a need for an improved full-length guidewire lumen catheter device and method of use which enables exchange over a conventional-length guidewire without the use of extension guidewires or exchange wires.

OBJECTS OF THE INVENTION

It is, therefore, a principal object of the present invention to provide a catheter and guidewire system which enables loading and unloading of the catheter over an indwelling, conventional length guidewire without compromising the position of the indwelling guidewire.

It is a further object of the present invention to provide a catheter and guidewire system which enables the exchange of a guidewire through the full-length guidewire lumen of an indwelling catheter.

Objects and advantages of the invention are set forth in part above and in part below. In addition, these and other objects and advantages of the invention will become apparent herefrom, or may be appreciated by practice with the invention, the same being realized and attained by means of instrumentalities, combinations and methods pointed out in the appended claims. Accordingly, the present invention resides in the novel parts, constructions, arrangements, improvements, methods and steps herein shown and described.

BRIEF DESCRIPTION OF THE INVENTION

In accordance with the present invention, an apparatus and method are provided for the exchange of a balloon catheter having a full-length guidewire lumen over an indwelling, conventional length guidewire.

The catheter device of the present invention includes an inflatable balloon member coupled at the distal portion of an elongated catheter shaft. The catheter shaft forms (1) an inflation lumen, which provides a flow passageway between the catheter shaft proximal end and the interior of the balloon member; (2) a guidewire lumen extending longitudinally throughout the catheter shaft; and (3) a hydraulic exchange lumen extending from the proximal end of the catheter shaft and terminating at a position proximate the distal end of the catheter shaft. A port is provided within the catheter shaft through which the distal portion of the hydraulic exchange lumen is in fluid communication with the guidewire lumen. A flow guiding member is disposed within the guidewire lumen to direct the flow of fluid passing from the hydraulic exchange lumen in a proximal direction through the guidewire lumen.

In a preferred embodiment, the catheter shaft comprises a three-lumen proximal shaft segment detachably coupled to a two-lumen distal shaft segment. In addition, the flow guiding member comprises a tube having a distal end sealingly coupled to the interior wall defining the guidewire lumen at a position distal of the port. The side wall of the flow guiding member extends across the port and terminates at its proximal end at a position proximal the port.

In another embodiment, the flow guiding member comprises a narrowed cross-sectional diameter within the guidewire lumen at a position distal of the port.

BRIEF DESCRIPTION OF THE DRAWINGS

The invention will be further described, by way of example, with reference to the accompanying drawings, wherein:

FIG. 1 is a longitudinal cross-sectional view of a basic embodiment of the catheter apparatus of the present invention;

FIG. 2 is a cross-sectional view of the catheter apparatus shown in FIG. 1 taken along line 2—2;

FIG. 3 is a cross-sectional view of the catheter apparatus shown in FIG. 1 taken along line 3—3;

FIG. 4 is a longitudinal cross-sectional view of an alternative embodiment of the catheter apparatus of the present invention;

FIG. 5 is a cross-sectional view of the catheter apparatus shown in FIG. 4 taken along line 5—5;

FIG. 6 is a cross-sectional view of the catheter apparatus shown in FIG. 4 taken along line 6—6;

FIG. 7 is a longitudinal cross-sectional view of another alternative embodiment of the catheter apparatus of the present invention;

FIG. 8 is a cross-sectional view of the catheter apparatus shown in FIG. 7 taken along line 8—8; and FIG. 9 is a cross-sectional view of the catheter apparatus shown in FIG. 7 taken along line 9—9.

DESCRIPTION OF THE PREFERRED EMBODIMENTS

It should be noted that while the following description will be specifically provided in the context of coronary angioplasty dilatation catheters, the invention is not so limited and is applicable to other catheter assemblies and procedures. For example, it will be understood that the present invention also applies to drug delivery and stent delivery catheters.

Referring generally to the embodiments of the invention shown in the accompanying drawings, wherein like reference numbers refer to like parts throughout the various views, the basic principles of the broadest aspects of the invention can be appreciated from FIGS. 1–3.

The hydraulic exchange catheter of the present invention, which is designated generally as 10, is illustrated in a basic form in FIG. 1. As here embodied, the hydraulic exchange catheter comprises an elongated, flexible catheter shaft 20 having a proximal end 22 and a distal end 24. A balloon member 26 is disposed near the distal end of catheter shaft 20. Balloon member 26 may be formed from polyvinyl chloride, polyethylene, polyurethane or preferably, polyethylene terephthalate.

The balloon member 26 may be inflated and deflated through an inflation lumen 30 formed in the catheter shaft 20. The inflation lumen 30 extends longitudinally through the length of the catheter shaft 20 from an open proximal end 32 to an open distal end 34 coupled in communication with the interior of balloon member 26. Fitting 36 is coupled to the proximal end of catheter shaft 20 in communication with inflation lumen 30. Fitting 36, preferably in the form a female luer, is designed to be connected to a suitable source of pressurized fluid or suction to enable inflation or deflation of balloon member 26.

Catheter shaft 20 also includes a guidewire lumen 40, which extends longitudinally throughout the entire length of the catheter shaft from an open proximal end 42 to an open distal end 44. Guidewire lumen 40 is dimensioned to slidably receive a standard coronary angioplasty guidewire (not shown). A fitting 46, preferably in the form of a female luer, is coupled to the proximal end of catheter shaft 20 and is in fluid communication with guidewire lumen 40. Fitting 46 is designed to enable sealing engagement with a suitable source of pressurized fluid.

As further shown in FIG. 1, catheter shaft 20 includes a hydraulic exchange lumen 50. Hydraulic exchange lumen 50 extends longitudinally from an open proximal end 52 to a closed distal end 54, wherein distal end 54 terminates at a position short of the distal end of catheter shaft 20. Hydraulic exchange lumen 50 is in fluid communication with guidewire lumen 40 via a port 58 located adjacent the distal end of hydraulic exchange lumen 50. Hydraulic exchange lumen 50 is in fluid communication with fitting 56. Fitting 56, preferably in the form of a female luer, is designed to enable sealing engagement with a suitable source of pressurized fluid.

Catheter shaft 20 further includes a flow guiding tube 48 disposed within guidewire lumen 40. Flow guiding tube 48 functions to redirect the distal flow of pressurized fluid traveling through hydraulic exchange lumen 50 in a proximal direction through guidewire lumen 40 after passing through port 58. By redirecting the flow of pressurized fluid in this manner, the pressurized fluid imparts a proximal force on the closed distal end of hydraulic exchange lumen 50 which causes catheter 10 to advance over the guidewire. As shown in FIG. 1, the outside wall of flow guiding tube 48 is sealingly coupled to the inside wall of the catheter shaft 20 forming guidewire lumen 40 at a position distal of port 58. The side wall of flow guiding tube 48 extends across port 58, and terminates at a position within guidewire lumen 40 proximal of port 58. The cross-sectional diameter of flow guiding tube 48 is slightly less than the cross-sectional diameter of guidewire lumen 40, such that there exists an annular space therebetween to form a restricted flow passageway from port 58 to guidewire lumen 40.

Inflation lumen 30, guidewire lumen 40 and hydraulic exchange lumen 50 may be disposed in either coaxial or side-by-side arrangement, or any combination thereof. FIG. 2 shows one of many alternative arrangements wherein the inflation lumen 30, guidewire lumen 40 and hydraulic exchange lumen 50 may be disposed in side-by-side or parallel arrangement within the proximal portion of catheter shaft 20.

Similarly, inflation lumen 30 and guidewire lumen 40 may be disposed within the distal portion of catheter shaft 20 in coaxial or side-by-side arrangement, or any combination thereof. FIG. 3 depicts inflation lumen 30 and guidewire lumen 40 in side-by-side arrangement within catheter shaft 20.

According to the basic principles of the present invention, operation and use of the hydraulic exchange device described in FIG. 1 is described as follows. A guiding catheter (not shown in FIGS.) is inserted into the patient's vasculature in a conventional manner. A Tuohy-Borst adapter (not shown in FIGS.) is then disposed at the proximal end of the guiding catheter and maintained at a position outside the patient's body. Next, the Tuohy-Borst adapter is opened to receive a standard length guidewire. The guidewire is routed through the patient's vasculature such that the distal portion of the guidewire is positioned across the treatment site. The Tuohy-Borst adapter is closed such that it locks onto the guidewire and thereby fixes the position of the distal portion of the guidewire across the treatment site. The proximal end of the guidewire is then loaded onto the distal end of the catheter through guidewire lumen 40. The catheter is advanced over the guidewire until the catheter distal end is adjacent the Tuohy-Borst adapter. Next, the administering physician attaches a syringe filled with saline (not shown) to fitting 56. After opening the Tuohy-Borst adapter, the administering physician injects the saline from the syringe into hydraulic exchange lumen 50 under steady and constant pressure. Pressurization of the hydraulic exchange lumen 50 in this manner exerts a distal force on catheter 10, thereby advancing catheter 10 through the patient's vasculature over the guidewire without effecting the position of the guidewire. The administering physician continues injecting saline into fitting 56 until the proximal end of the guidewire protrudes through the proximal end of guidewire lumen 40. While holding the proximal end of the guidewire, the administering physician pushes the proximal end of the catheter toward the Tuohy-Borst adapter until balloon member 26 is positioned across the treatment site.

Once balloon member 26 has been positioned across the treatment site, pressurized inflation fluid may be injected through fitting 36 by the use of any pressurizing device known in the art (not shown in the FIGS.). The inflation fluid passes through fitting 36 and inflation lumen 30, and into balloon member 26. The inflation of balloon member 26 can be observed if radiographic contrast liquid is used as the inflation fluid. As balloon member 26 is inflated with pressurized inflation fluid, it presses against the treatment site and dilates the stenosis.

During a catheterization procedure, it may be necessary to exchange the indwelling catheter with another catheter having a different feature. For example, it may be desired to follow a balloon dilatation procedure with a drug delivery or stent delivery procedure. Likewise, in the event the balloon on the indwelling catheter is too small to sufficiently dilate the stenosis, the administering physician may elect to exchange the indwelling catheter with another catheter having a larger balloon. As set forth below, the present invention provides a means for catheter exchange without the use of an extension wire or an exchange wire.

While holding the proximal end of the guidewire in one hand, the administering physician grasps and withdraws the proximal end of the indwelling catheter until the proximal end of the guidewire is positioned within fitting 46. Next, the administering physician attaches a syringe filled with saline (not shown) to fitting 46 and injects saline into guidewire lumen 40 under steady and constant pressure. The injection of saline into the guidewire lumen 40 in this manner causes catheter 10 to move in a proximal direction, without effecting the position of the guidewire. The administering physician continues injecting saline into fitting 46 until the distal end of catheter 13 has exited the Tuohy-Borst adapter. While maintaining the distal end of the guidewire across the treatment site by holding the guidewire at a position immediately adjacent the Tuohy-Borst adapter or closing the Tuohy-Borst adapter such that it locks onto the guidewire, the administering physician removes catheter 10 from the proximal end of the guidewire.

After the original catheter is removed, a second catheter in the form of the present invention having a different size balloon may be threaded onto and advanced over the guidewire as described above.

According to an alternative form of the present invention illustrated in FIG. 4, the catheter comprises a detachable two-part catheter tube. As here embodied, catheter 10 includes a three-lumen proximal shaft 60, a two-lumen distal shaft 80, a balloon member 100, and a flow guiding tube 110.

The proximal shaft 60 has a proximal end 62 and a distal end 64, and includes an inflation lumen 66, a guidewire lumen 70 and a hydraulic exchange lumen 74. Inflation lumen 66 extends longitudinally throughout the length of proximal shaft 60 from an open proximal end 67 to an open distal end 68, and forms a continuous pathway for the flow of inflation fluid therebetween. Guidewire lumen 70 also extends longitudinally throughout the length of proximal shaft 60 from an open proximal end 71 to an open distal end 72. Guidewire lumen 70 is dimensioned to slidably receive a standard coronary angioplasty guidewire. Hydraulic exchange lumen 74 extends longitudinally through proximal shaft 60 from an open proximal end 75 and terminates at a closed distal end 76. Hydraulic exchange lumen 74 is in fluid communication with guidewire lumen 70 via a port 78 located adjacent the distal end of hydraulic exchange lumen 74.

As shown in FIG. 4, the proximal ends of inflation lumen 66, guidewire lumen 70 and hydraulic exchange lumen 74 are in fluid communication with fittings 69, 73 and 77, respectively. Each of the fittings 69, 73, and 77 are preferably in the form of a female luer designed to enable sealing engagement with a suitable source of pressurized fluid.

The distal shaft 80 has a proximal end 82 and a distal end 84, and includes an inflation extension lumen 90 and a guidewire extension lumen 94. Inflation extension lumen 90 extends longitudinally through distal shaft 80 from an open proximal end 91 to and open distal end 92. Similarly, guidewire extension lumen 94 extends longitudinally through distal shaft 80 from an open proximal end 95 to an open distal end 96.

As illustrated in FIG. 4, the proximal end 82 of distal shaft 80 is coupled to the distal end 64 of proximal shaft 60. Further, inflation extension lumen 90 and guidewire extension lumen 94 are in fluid communication with inflation lumen 66 and guidewire lumen 70 of proximal shaft 60, respectively.

Balloon member 100 is disposed at the distal end of distal shaft 80, and is in fluid communication with the distal end of inflation extension lumen 90. To this end, balloon member 100 may be inflated by injecting pressurized inflation fluid through fitting 69, inflation lumen 66 and inflation extension lumen 90, and into balloon member 100. Similarly, balloon member 100 may be deflated by purging the inflation fluid from balloon member 100 through inflation extension lumen 90, inflation lumen 66 and fitting 69.

The flow guiding tube 110 is disposed within guidewire lumen 70. Flow guiding tube 110 functions to redirect the distal flow of pressurized fluid traveling through hydraulic exchange lumen 74 in a proximal direction through guidewire lumen 70 after passing through port 78. To this end, the outside wall of flow guiding tube 110 is sealingly coupled to the inside wall of proximal shaft 60 defining guidewire lumen 70 at a position distal of port 78. The side wall of flow guiding tube 110 extends across port 78, and terminates at a position within guidewire lumen 70 proximal of port 78. The cross-sectional diameter of flow guiding tube 110 is slightly less than the cross-sectional diameter of guidewire lumen 70, such that there exists an annular space therebetween to form a restricted flow passageway from port 78 to guidewire lumen 70.

Inflation lumen 66, guidewire lumen 70 and hydraulic exchange lumen 74 may be disposed within proximal shaft 60 in either coaxial or side-by-side arrangement, or any combination thereof. For example, as shown in FIG. 5, guidewire lumen 70 and hydraulic exchange lumen 74 may be coaxially disposed relative to one another an in side-by-side arrangement with inflation lumen 66.

In addition, inflation extension lumen 90 and guidewire extension lumen 94 may be disposed within distal shaft 80 in either coaxial or side-by-side arrangement, or any combination thereof. As shown in FIG. 6, inflation extension lumen 90 and guidewire extension lumen 94 are disposed in side-by-side arrangement within distal shaft 80.

In another alternative form of the present invention illustrated in FIG. 7, the flow guiding tube is replaced with a lumen narrowing disposed within the guidewire lumen. As here embodied, catheter 10 includes a three-lumen proximal shaft 60, a two-lumen distal shaft 80, a balloon member 100, and lumen narrowing 120.

The proximal shaft 60 has a proximal end 62 and a distal end 64, and includes an inflation lumen 66, a guidewire lumen 70 and a hydraulic exchange lumen 74. Inflation lumen 66 extends longitudinally throughout the length of proximal shaft 60 from an open proximal end 67 to an open distal end 68, and forms a continuous pathway for the flow of inflation fluid therebetween. Guidewire lumen 70 also extends longitudinally throughout the length of proximal shaft 60 from an open proximal end 71 to an open distal end 72. Guidewire lumen 70 is dimensioned to slidably receive a standard coronary angioplasty guidewire. Hydraulic exchange lumen 74 extends longitudinally through proximal shaft 60 from an open proximal end 75 and terminates at a closed distal end 76. Hydraulic exchange lumen 74 is coupled in fluid communication with guidewire lumen 70 via a port 78 located adjacent the distal end of hydraulic exchange lumen 74.

As shown in FIG. 7, the proximal ends of inflation lumen 66, guidewire lumen 70 and hydraulic exchange lumen 74 are in fluid communication with fittings 69, 73 and 77, respectively. Each of the fittings 69, 73, and 77 are preferably in the form of a female luer designed to provide sealing engagement with a suitable source of pressurized fluid.

The distal shaft 80 has a proximal end 82 and a distal end 84, and includes a inflation extension lumen 90 and a guidewire extension lumen 94. Inflation extension lumen 90 extends longitudinally through distal shaft 80 from an open proximal end 91 to and open distal end 92. Similarly, guidewire extension lumen 94 extends longitudinally through distal shaft 80 from an open proximal end 95 to an open distal end 96.

As illustrated in FIG. 7, the proximal end 82 of distal shaft 80 is coupled to the distal end 64 of proximal shaft 60. Further, inflation extension lumen 90 and guidewire extension lumen 94 are aligned in fluid communication with inflation lumen 66 and guidewire lumen 70 of proximal shaft 60, respectively.

Balloon member 100 is disposed at the distal end of distal shaft 80, and is coupled in fluid communication with the distal end of inflation extension lumen 90. To this end, balloon member 100 may be inflated by injecting pressurized inflation fluid through fitting 69, inflation lumen 66 and inflation extension lumen 90, and into balloon member 100. Similarly, balloon member 100 may be deflated by purging the inflation fluid from balloon member 100 through inflation extension lumen 90, inflation lumen 66 and fitting 69.

The lumen narrowing 120 is disposed within guidewire lumen 70 and/or guidewire extension lumen 94 at a position distal of port 78. Preferably, lumen narrowing 120 spans across the joint coupling the distal end of proximal shaft 60 and the proximal end of distal shaft 80. As shown in FIG. 7, lumen narrowing 120 forms a narrowing within guidewire lumen 70, which provides a restricted pathway for the distal flow of pressurized fluid passing from hydraulic exchange lumen 74, through port 78 and into guidewire lumen 70. Preferably, lumen narrowing 120 includes an bore having a cross-sectional diameter of about 0.016 inches and guidewire lumen 70 has a cross-sectional diameter of about 0.020 inches. According to this configuration, lumen narrowing 120 functions to limit the distal flow and enables the proximal flow of pressurized fluid traveling from hydraulic exchange lumen 74, through port 78 and into guidewire lumen 70.

Inflation lumen 66, guidewire lumen 70 and hydraulic exchange lumen 74 may be disposed within proximal shaft 60 in either coaxial or side-by-side arrangement, or any combination thereof. For example, as shown in FIG. 8, inflation lumen 66 and hydraulic exchange lumen 74 are in the form of abutting C-shaped lumens which adjoin coaxial with guidewire lumen 70. Similarly, inflation extension lumen 90 and guidewire extension lumen 94 may be disposed within distal shaft 80 in coaxial or side-by-side arrangement, or any combination thereof. As shown in FIG. 9, inflation extension lumen 90 and guidewire extension lumen 94 are coaxially disposed within distal shaft 80.

Each of the alternative embodiments shown in FIGS. 4–6 and FIGS. 7–9 may be advanced or withdrawn over an indwelling conventional-length guidewire in the same manner as described above with respect to the basic embodiment shown in FIGS. 1–3.

While only a few embodiments have been illustrated and described in connection with the present invention, various modifications and changes in both the apparatus and method will become apparent to those skilled in the art. For example, it will be understood that the alternative embodiment of the present invention illustrated in FIG. 7 may be modified to comprise a catheter having a one-piece catheter shaft. Moreover, the narrowed cross-sectional diameter within the guidewire catheter formed by the lumen narrowing in the alternative embodiment shown in FIG. 7 may instead be formed by a catheter shaft wall having varying thickness. All such modifications or changes falling within the scope of the claims are intended to be included therein.

We claim:

1. A catheter device adapted for use with a conventional length guidewire, comprising:

(a) an elongated, flexible shaft having a proximal section and a distal section, the shaft defining (i) an inflation lumen extending longitudinally through the shaft from an open proximal end formed at the proximal section of the shaft to an open distal end formed at the distal section of the shaft;

(ii) a guidewire lumen extending longitudinally through the shaft from an open proximal end formed at the proximal section of the shaft to an open distal end formed at the distal section of the shaft;

(iii) a hydraulic exchange lumen extending longitudinally through the shaft from an open proximal end formed at the shaft proximal section to a closed distal end terminating proximal the distal section of the shaft, the hydraulic exchange lumen having an outlet port proximal its closed distal end through which it is in fluid communication with the guidewire lumen;

(b) a balloon member coupled to the distal section of the shaft, the balloon member defining an interior cavity in fluid communication with the distal end of the inflation lumen;

(c) a flow guiding member disposed within the guidewire lumen, wherein the flow guiding member is adapted to redirect the distal flow of pressurized fluid traveling through the hydraulic exchange lumen in a proximal direction through the guidewire lumen.

2. The catheter device of claim 1, which further comprises a first fitting in fluid communication with the inflation lumen, a second fitting in fluid communication with the guidewire lumen and a third fitting in fluid communication with the hydraulic exchange lumen, wherein each fitting is adapted to enable fluid communication with a source of pressurized fluid.

3. The catheter device of claim 1, wherein the flow guiding member comprises a tube disposed longitudinally within the guidewire lumen and having an open distal end coupled within the guidewire lumen at a position distal of the outlet end port and an open proximal end positioned proximal of the outlet port.

4. The catheter device of claim 1, wherein the flow guiding member comprises a reduced diameter section within the guidewire lumen at a position distal of the outlet port.

5. A catheter device adapted for use with a conventional length guidewire, comprising:

(a) a proximal shaft segment having a proximal end and a distal end, the proximal shaft segment defining
  (i) an inflation lumen extending longitudinally through the proximal shaft segment from an open proximal end formed at the proximal end of the proximal shaft segment to an open distal end formed at the distal end of the proximal shaft segment;
  (ii) a guidewire lumen extending longitudinally through the proximal shaft segment from an open proximal end formed at the proximal of the proximal shaft segment to an open distal end formed at the distal end of the proximal shaft segment;
  (iii) a hydraulic exchange lumen extending longitudinally through the proximal shaft segment from an open proximal end formed at the proximal end of the proximal shaft segment to a closed distal end terminating proximal the distal end of the proximal shaft segment, the hydraulic exchange lumen having an outlet port proximal its closed distal end through which it is in fluid communication with the guidewire lumen;

(b) a distal shaft segment having a distal end and a proximal end coupled to the distal end of the proximal shaft segment, the distal shaft segment defining
  (i) an inflation extension lumen extending longitudinally through the distal shaft segment from an open proximal end formed at the proximal end of the distal shaft segment to an open distal end formed at the distal end of the distal shaft segment, the inflation extension lumen being in fluid communication with the inflation lumen and forming a continuous flow passageway throughout;
  (ii) a guidewire extension lumen extending longitudinally through the distal shaft segment from an open proximal end formed at the proximal of the distal shaft segment to an open distal end formed at the distal end of the distal shaft segment, the guidewire extension lumen being in fluid communication with the guidewire lumen and forming a continuous flow passageway throughout;

(c) a balloon member coupled adjacent the distal end of the distal shaft segment, the balloon member defining an interior cavity in fluid communication with the distal end of the inflation extension lumen;

(d) a flow guiding member disposed within the guidewire lumen, wherein the flow guiding member is adapted to redirect the distal flow of pressurized fluid traveling through the hydraulic exchange lumen in a proximal direction through the guidewire lumen.

6. The catheter device of claim 5, which further comprises a first fitting in fluid communication with the inflation lumen, a second fitting in fluid communication with the guidewire lumen and a third fitting in fluid communication with the hydraulic exchange lumen, wherein each fitting is adapted to enable fluid communication with a source of pressurized fluid.

7. The catheter device of claim 5, wherein the flow guiding member comprises a tube disposed longitudinally within the guidewire lumen and having an open distal end coupled within the guidewire lumen at a position distal of the outlet end port and, an open proximal end positioned proximal of the outlet port.

8. The catheter device of claim 5, wherein the flow guiding member comprises a reduced diameter section within the guidewire lumen at a position distal of the outlet port.

9. The catheter device of claim 5, wherein the flow guiding member comprises a reduced diameter section formed within the guidewire extension lumen at a position distal of the outlet port.

10. The catheter device of claim 9, wherein the reduced diameter section is formed by a lumen narrowing disposed within the guidewire extension lumen.

11. The catheter device of claim 5, wherein the flow guiding member comprises a reduced diameter section formed by a lumen narrowing having a distal end extending into the proximal section of the guidewire extension lumen and a proximal end extending into the distal section of the guidewire lumen.

12. A method for loading a catheter device having a full-length guidewire lumen over a conventional-length guidewire without the use of an exchange guidewire or a guidewire extension, the catheter device comprising an elongated shaft having a proximal end, a distal end, the shaft defining an inflation lumen and a guidewire lumen extending longitudinally throughout its length, and a hydraulic exchange lumen extending from the shaft proximal end and terminating at a position proximal the shaft distal end, the hydraulic exchange lumen being in fluid communication with the guidewire lumen, a balloon member coupled adjacent the distal end of the shaft, the balloon member defining an interior cavity in fluid communication with the inflation lumen, and a flow guiding member disposed within the guidewire lumen for redirecting the distal flow of pressurized fluid traveling through the hydraulic exchange lumen in a proximal direction through the guidewire lumen, the method comprising the steps of:

(a) inserting a guiding catheter in a patient's vasculature;
(b) disposing an adapter at the proximal end of the guiding catheter at a position outside the patient;
(c) opening the adapter and inserting a conventional length guidewire having a distal end and a proximal end into the guiding catheter and advancing the distal end of the guidewire to a treatment site within the patient's vasculature;
(d) maintaining the distal end of the guidewire across the treatment site and loading the distal end of the catheter guidewire lumen over the proximal end of the guidewire and advancing the catheter through the adapter into the guiding catheter;

(e) advancing the catheter over the guidewire until the distal end of the catheter is immediately proximal the adapter;

(f) injecting fluid into the proximal end of the hydraulic exchange lumen under constant and steady pressure, thereby advancing the catheter over the guidewire into the patient's vasculature until the proximal end of the guidewire protrudes from the proximal end of the guidewire lumen;

(g) gripping the proximal end of the guidewire and grasping and pushing the catheter toward the adapter until the balloon member is positioned across the treatment site.

13. A method for loading and unloading a catheter device having a full-length guidewire lumen over a conventional-length guidewire without the use of an exchange guidewire or a guidewire extension, the catheter device comprising an elongated shaft having a proximal end, a distal end, the shaft defining an inflation lumen and a guidewire lumen extending longitudinally throughout its length, and a hydraulic exchange lumen extending from the shaft proximal end and terminating at a position proximal the shaft distal end, the hydraulic exchange lumen being in fluid communication with the guidewire lumen, a balloon member coupled adjacent the distal end of the shaft, the balloon member defining an interior cavity in fluid communication with the inflation lumen, and a flow guiding member disposed within the guidewire lumen for redirecting the distal flow of pressurized fluid traveling through the hydraulic exchange lumen in a proximal direction through the guidewire lumen, the method comprising the steps of:

(a) inserting a guiding catheter in a patient's vasculature;

(b) disposing an adapter at the proximal end of the guiding catheter at a position outside the patient;

(c) opening the adapter and inserting a conventional length guidewire having a distal end and a proximal end into the guiding catheter and advancing the distal end of the guidewire to a treatment site within the patient's vasculature;

(d) maintaining the distal end of the guidewire across the treatment site and loading the distal end of the catheter guidewire lumen into the proximal end of the guidewire and advancing the catheter through the adapter into the guiding catheter;

(e) advancing the catheter over the guidewire until the distal end of the catheter is immediately proximal the adapter;

(f) injecting fluid into the proximal end of the hydraulic exchange lumen under constant and steady pressure, thereby advancing the catheter over the guidewire into the patient's vasculature until the proximal end of the guidewire protrudes from the proximal end of the guidewire lumen;

(g) gripping the proximal end of the guidewire and grasping and pushing the catheter toward the adapter until the balloon member is positioned across the treatment site;

(h) gripping the proximal end of the guidewire lumen and grasping and withdrawing the catheter from the patient until the proximal end of the catheter is positioned within the proximal end of the guidewire lumen;

(i) injecting fluid into the proximal end of the guidewire lumen under constant and steady pressure, thereby withdrawing the catheter from the patient's vasculature over the guidewire until the distal end of the catheter is immediately proximal the adapter;

(j) maintaining the position of the distal end of the guidewire across the treatment site and grasping and removing the catheter from the proximal end of the guidewire.

* * * * *